United States Patent
Klebanov et al.

(10) Patent No.: US 10,874,320 B2
(45) Date of Patent: Dec. 29, 2020

(54) DISPLAY OF MULTIPLE ELECTROGRAMS ANATOMICAL MAP

(71) Applicant: Boston Scientific Scimed Inc., Maple Grove, MN (US)

(72) Inventors: Daniel Klebanov, Arlington, MA (US); Stefano Capellino, Toulouse (FR); Vasiliy E. Buharin, Arlington, MA (US); Brian Stewart, North Reading, MA (US); Arun Ramasamy, Arlington, MA (US); Nathan H. Bennett, Cambridge, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 171 days.

(21) Appl. No.: 16/149,399

(22) Filed: Oct. 2, 2018

(65) Prior Publication Data

US 2019/0099098 A1 Apr. 4, 2019

Related U.S. Application Data

(60) Provisional application No. 62/566,666, filed on Oct. 2, 2017.

(51) Int. Cl.
*A61B 5/044* (2006.01)
*G06T 3/40* (2006.01)
(Continued)

(52) U.S. Cl.
CPC ............ *A61B 5/044* (2013.01); *A61B 5/042* (2013.01); *A61B 5/04012* (2013.01);
(Continued)

(58) Field of Classification Search
CPC .. G06K 9/00; A61B 5/042; A61B 5/00; A61B 5/044; A61B 5/06;
(Continued)

(56) References Cited

U.S. PATENT DOCUMENTS 6,070,094 A   5/2000 Swanson et al.
6,233,491 B1  5/2001 Kordis et al.
(Continued)

OTHER PUBLICATIONS

International Search Report and Written Opinion issued in PCT/US2018/053881, dated Dec. 19, 2018, 11 pages.

*Primary Examiner* — Jon Eric C Morales
(74) *Attorney, Agent, or Firm* — Faegre Drinker Biddle & Reath LLP (57) ABSTRACT

A system includes a display device configured to present a cardiac map; and a processing unit configured to: receive electrical signals; generate the cardiac map; and facilitate display of the cardiac map, where each electrical signal corresponds to a map location. The processing unit is also configured to receive a user selection of a selected portion of the cardiac map, the selected portion including a set of map locations, each of the set of map locations corresponding to an electrical signal of a set of signals that is a subset of the received electrical signals. The set of map locations has a first spatial arrangement and the processing unit is configured to facilitate display of a set of electrical signal representations, each representation corresponding to one of the set of electrical signals, the set of electrical signal representations having a second spatial arrangement, which corresponds to the first spatial arrangement.

18 Claims, 5 Drawing Sheets

(51) Int. Cl.
    *A61B 5/00*            (2006.01)
    *A61B 5/04*            (2006.01)
    *G06F 3/0488*        (2013.01)
    *A61B 5/042*          (2006.01)

(52) U.S. Cl.
    CPC .......... *A61B 5/7435* (2013.01); *A61B 5/7475* (2013.01); *G06F 3/04883* (2013.01); *G06T 3/40* (2013.01)

(58) Field of Classification Search
    CPC ...... A61B 2018/00839; A61B 18/1492; A61B 2018/0057; A61B 2562/043; A61B 2576/023; A61B 34/20; A61B 34/25; A61B 5/0036; A61B 5/0044; A61B 5/04017; A61B 5/04021; A61B 5/0422; A61B 5/0452; A61B 5/0538; A61B 5/065; A61B 5/066; A61B 5/068; A61B 5/4836; A61B 5/6852; A61B 5/6855; G16H 30/40; G16H 50/50
    USPC .................................. 600/373–374; 382/128
    See application file for complete search history.

(56) References Cited

U.S. PATENT DOCUMENTS

| | | | |
|---|---|---|---|
| 6,735,465 | B2 | 5/2004 | Panescu |
| 8,428,700 | B2 | 4/2013 | Harlev et al. |
| 8,615,287 | B2 | 12/2013 | Harlev et al. |
| 8,948,837 | B2 | 2/2015 | Harlev et al. |
| 2008/0194979 | A1 | 8/2008 | Madry et al. |
| 2010/0280399 | A1 | 11/2010 | Francis et al. |
| 2011/0206256 | A1 | 8/2011 | Ramanathan et al. |
| 2013/0274582 | A1 | 10/2013 | Afonso et al. |
| 2015/0065836 | A1 | 3/2015 | Thakur et al. |
| 2017/0202469 | A1 | 7/2017 | Scharf et al. |

DISPLAY OF MULTIPLE ELECTROGRAMS ANATOMICAL MAP

CROSS-REFERENCE TO RELATED APPLICATION

This application claims priority to Provisional Application No. 62/566,666, filed Oct. 2, 2017, which is herein incorporated by reference in its entirety.

TECHNICAL FIELD

The present disclosure relates to medical systems and methods for mapping an anatomical space of the body. More specifically, the disclosure relates to systems and methods for cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In both techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

Dense electro-anatomical mapping of endocardial surfaces generates maps with many thousands of points, where each point is associated with an electrogram. An electrogram is a recording of a physiological electrical activity at a given location on the endocardial surface, measured from a single electrode at a given point in time. An electrogram may be either unipolar or bipolar, depending on whether the measured voltage of the electrode is referenced against a stable reference potential or (one or more) adjacent electrode(s), respectively.

During map review, it is common for the user to inspect individual electrograms to assess tissue pathology. This is normally done either by clicking on a representation of an electrogram (which may be represented by a raised bump on a map) or by dragging a virtual probe tool across the surface of the map. In the latter case, the displayed electrogram representation is typically based on the electrode which is nearest to the location of the probe. Due to the large number of electrograms in the map, however, this can be time-consuming and, in some cases, impractical for reviewing individual electrograms and/or assessing an electrogram's characteristics in the context of its neighbors.

SUMMARY

Embodiments of the subject matter disclosed herein include a tool that facilitates dynamically and concurrently displaying MULTIPLE electrogram representations. The user interacts with a GUI by selecting a selected portion of the cardiac map on the surface of the mesh using a probe-like drawing tool. MULTIPLE electrograms, corresponding to points along the user-selected area, are displayed simultaneously and sorted spatially in a manner that corresponds to the corresponding map location representations. The user can manipulate the selection, causing the electrogram representations to update dynamically.

In an Example 1, a system for facilitating display of cardiac information, the system comprising: a display device configured to present a cardiac map; and a processing unit configured to: receive a plurality of electrical signals; generate, based on the plurality of electrical signals, the cardiac map; facilitate display, via the display device, of the cardiac map, wherein each of the plurality of electrical signals corresponds to a cardiac map location; receive, from an input device, a user selection of a selected portion of the cardiac map, the selected portion comprising a set of map locations, each of the set of map locations corresponding to an electrical signal of a set of electrical signals, the set of map locations having a first spatial arrangement, wherein the set of electrical signals comprises a subset of the plurality of electrical signals; and facilitate display, via the display, of a set of electrical signal representations, each electrical signal representation of the set of electrical signal representations corresponding to one of the set of electrical signals, the set of electrical signal representations comprising a second spatial arrangement, wherein the second spatial arrangement corresponds to the first spatial arrangement.

In an Example 2, the system of Example 1, wherein each of the plurality of electrical signals comprises an electrogram.

In an Example 3, the system of either of Examples 1 or 2, wherein the processing unit is further configured to facilitate display, via the display device, of a selection indicator, the selection indicator comprising a representation of the selected portion of the map.

In an Example 4, the system of any of Examples 1-3, wherein the processing unit is further configured to: identify, based on the selected portion of the cardiac map, the set of electrical signals; determine the first spatial arrangement; and determine, based on the first spatial arrangement, the second spatial arrangement.

In an Example 5, the system of Example 4, wherein the processing unit is configured to determine the second spatial arrangement by performing a linear scaling operation based on the first spatial arrangement.

In an Example 6, the system of any of Examples 1-5, wherein the selected portion of the map comprises a curve, drawn using the input device, on the cardiac map.

In an Example 7, the system of any of Examples 1-5, wherein the selected portion of the map comprises a selected region of the cardiac map, and wherein the representation of the selected region comprises a grid having a plurality of grid cells arranged in a plurality of columns and a plurality of rows.

In an Example 8, the system of Example 7, wherein each electrical signal of the set of electrical signals has a map location corresponding to one of the plurality of grid cells.

In an Example 9, the system of any of Examples 1-5, wherein the processing unit is further configured to facilitate display, via the display device, of a plurality of electrical signal representations, each of the plurality of electrical signal representations corresponding to one of the plurality of electrical signals, wherein the selected portion of the map comprises a set of selected electrical signal representations.

In an Example 10, the system of any of Examples 1-9, wherein the processing unit is further configured to: receive, via the input device, a user input associated with a movement, from a first position to a second position, of the selection indicator; determine, based on the user input, an additional selected portion of the cardiac map, the additional selected portion comprising an additional set of map locations, each of the additional set of map locations corresponding to an electrical signal of an additional set of electrical signals, the additional set of map locations having a third spatial arrangement, wherein the additional set of electrical signals comprises an additional subset of the plurality of electrical signals; and facilitating display, via the display, of an additional set of electrical signal representations, each electrical signal representation of the additional set of electrical signal representations corresponding to one of the additional set of electrical signals, the additional set of electrical signal representations comprising a fourth spatial arrangement, wherein the fourth spatial arrangement corresponds to the third spatial arrangement.

In an Example 11, the system of any of Examples 1-9, wherein the processing unit is further configured to: receive, via the input device, a user selection of an additional selected portion of the cardiac map; determine, based on the user input, an additional selected portion of the cardiac map, the additional selected portion comprising an additional set of map locations, each of the additional set of map locations corresponding to an electrical signal of an additional set of electrical signals, the additional set of map locations having a third spatial arrangement, wherein the additional set of electrical signals comprises an additional subset of the plurality of electrical signals; and facilitating display, via the display, of an additional set of electrical signal representations simultaneously with the display of the set of electrical signal representations, each electrical signal representation of the additional set of electrical signal representations corresponding to one of the electrical signal set of electrical signals, the additional set of electrical signal representations comprising a fourth spatial arrangement, wherein the fourth spatial arrangement corresponds to the third spatial arrangement.

In an Example 12, the system of Example 11, wherein the set of electrical signal representations is displayed in a first column and the additional set of electrical signal representations is displayed in a second column, and wherein the second column is displayed adjacent the first column.

In an Example 13, a method of presenting cardiac information, the method comprising: receiving a plurality of electrical signals; generating, based on the plurality of electrical signals, the cardiac map; facilitating display, via the display device, of the cardiac map, wherein each of the plurality of electrical signals corresponds to a cardiac map location; receiving, from an input device, a user selection of a selected portion of the cardiac map, the selected portion comprising a set of map locations, each of the set of map locations corresponding to an electrical signal of a set of electrical signals, the set of map locations having a first spatial arrangement, wherein the set of electrical signals comprises a subset of the plurality of electrical signals; and facilitating display, via the display device, of a set of electrical signal representations, each electrical signal representation of the set of electrical signal representations corresponding to one of the set of electrical signals, the set of electrical signal representations comprising a second spatial arrangement, wherein the second spatial arrangement corresponds to the first spatial arrangement.

In an Example 14, the method of Example 13, wherein the selected portion of the map comprises a curve, drawn using the input device, on the cardiac map.

In an Example 15, the method of Example 13, wherein the selected portion of the map comprises a selected region of the cardiac map, and wherein the representation of the selected region comprises a grid having a plurality of grid cells arranged in a plurality of columns and a plurality of rows.

In an Example 16, a system for facilitating display of cardiac information, the system comprising: a display device configured to present a cardiac map; and a processing unit configured to: receive a plurality of electrical signals; generate, based on the plurality of electrical signals, the cardiac map; facilitate display, via the display device, of the cardiac map, wherein each of the plurality of electrical signals corresponds to a cardiac map location; receive, from an input device, a user selection of a selected portion of the cardiac map, the selected portion comprising a set of map locations, each of the set of map locations corresponding to an electrical signal of a set of electrical signals, the set of map locations having a first spatial arrangement, wherein the set of electrical signals comprises a subset of the plurality of electrical signals; and facilitate display, via the display, of a set of electrical signal representations, each electrical signal representation of the set of electrical signal representations corresponding to one of the set of electrical signals, the set of electrical signal representations comprising a second spatial arrangement, wherein the second spatial arrangement corresponds to the first spatial arrangement.

In an Example 17, the system of Example 16, wherein each of the plurality of electrical signals comprises an electrogram.

In an Example 18, the system of Example 16, wherein the processing unit is further configured to facilitate display, via the display device, of a selection indicator, the selection indicator comprising a representation of the selected portion of the map.

In an Example 19, the system of Example 16, wherein the processing unit is further configured to: identify, based on the selected portion of the cardiac map, the set of electrical signals; determine the first spatial arrangement; and determine, based on the first spatial arrangement, the second spatial arrangement.

In an Example 20, the system of Example 19, wherein the processing unit is configured to determine the second spatial arrangement by performing a linear scaling operation based on the first spatial arrangement.

In an Example 21, the system of Example 16, wherein the selected portion of the map comprises a curve, drawn using the input device, on the cardiac map.

In an Example 22, the system of Example 16, wherein the selected portion of the map comprises a selected region of the cardiac map, and wherein the representation of the selected region comprises a grid having a plurality of grid cells arranged in a plurality of columns and a plurality of rows.

In an Example 23, the system of Example 22, wherein each electrical signal of the set of electrical signals has a map location corresponding to one of the plurality of grid cells.

In an Example 24, the system of Example 16, wherein the processing unit is further configured to facilitate display, via the display device, of a plurality of electrical signal representations, each of the plurality of electrical signal representations corresponding to one of the plurality of electrical signals, wherein the selected portion of the map comprises a set of selected electrical signal representations.

In an Example 25, the system of Example 16, wherein the processing unit is further configured to: receive, via the input device, a user input associated with a movement, from a first position to a second position, of the selection indicator; determine, based on the user input, an additional selected portion of the cardiac map, the additional selected portion comprising an additional set of map locations, each of the additional set of map locations corresponding to an electrical signal of an additional set of electrical signals, the additional set of map locations having a third spatial arrangement, wherein the additional set of electrical signals comprises an additional subset of the plurality of electrical signals; and facilitating display, via the display, of an additional set of electrical signal representations, each electrical signal representation of the additional set of electrical signal representations corresponding to one of the additional set of electrical signals, the additional set of electrical signal representations comprising a fourth spatial arrangement, wherein the fourth spatial arrangement corresponds to the third spatial arrangement.

In an Example 26, the system of Example 16, wherein the processing unit is further configured to: receive, via the input device, a user selection of an additional selected portion of the cardiac map; determine, based on the user input, an additional selected portion of the cardiac map, the additional selected portion comprising an additional set of map locations, each of the additional set of map locations corresponding to an electrical signal of an additional set of electrical signals, the additional set of map locations having a third spatial arrangement, wherein the additional set of electrical signals comprises an additional subset of the plurality of electrical signals; and facilitating display, via the display, of an additional set of electrical signal representations simultaneously with the display of the set of electrical signal representations, each electrical signal representation of the additional set of electrical signal representations corresponding to one of the electrical signal set of electrical signals, the additional set of electrical signal representations comprising a fourth spatial arrangement, wherein the fourth spatial arrangement corresponds to the third spatial arrangement.

In an Example 27, the system of Example 26, wherein the set of electrical signal representations is displayed in a first column and the additional set of electrical signal representations is displayed in a second column, and wherein the second column is displayed adjacent the first column.

In an Example 28, a method of presenting cardiac information, the method comprising: receiving a plurality of electrical signals; generating, based on the plurality of electrical signals, the cardiac map; facilitating display, via the display device, of the cardiac map, wherein each of the plurality of electrical signals corresponds to a cardiac map location; receiving, from an input device, a user selection of a selected portion of the cardiac map; identifying a set of map locations corresponding to the selected portion; identifying, for each of the set of map locations, a corresponding electrical signal of a set of electrical signals, the set of map locations having a first spatial arrangement, wherein the set of electrical signals comprises a subset of the plurality of electrical signals; and facilitating display, via the display device, of a set of electrical signal representations, each electrical signal representation of the set of electrical signal representations corresponding to one of the set of electrical signals, the set of electrical signal representations comprising a second spatial arrangement, wherein the second spatial arrangement corresponds to the first spatial arrangement.

In an Example 29, the method of Example 28, wherein each of the plurality of electrical signals comprises an electrogram.

In an Example 30, the method of Example 28, further comprising facilitating display, via the display device, of a selection indicator, the selection indicator comprising a representation of the selected portion of the map.

In an Example 31, the method of Example 28, further comprising: determining the first spatial arrangement; and determining, based on the first spatial arrangement, the second spatial arrangement.

In an Example 32, the method of Example 31, further comprising determining the second spatial arrangement by performing a linear scaling operation based on the first spatial arrangement.

In an Example 33, the method of Example 28, wherein the selected portion of the map comprises at least one of (1) a curve, drawn using the input device, on the cardiac map; (2) a selected region of the cardiac map, and wherein the representation of the selected region comprises a grid having a plurality of grid cells arranged in a plurality of columns and a plurality of rows, wherein each electrical signal of the set of electrical signals has a map location corresponding to one of the plurality of grid cells; and (3) a set of selected electrical signal representations, wherein the cardiac map includes a plurality of electrical signal representations, each of the plurality of electrical signal representations corresponding to one of the plurality of electrical signals.

In an Example 34, a system for facilitating display of cardiac information, the system comprising: a display device configured to present a cardiac map; and a processing unit configured to: receive a plurality of electrical signals; generate, based on the plurality of electrical signals, the cardiac map; facilitate display, via the display device, of the cardiac map, wherein each of the plurality of electrical signals corresponds to a cardiac map location; receive, from an input device, a user selection of a first selected portion of the cardiac map, the first selected portion comprising a first set of map locations, each of the first set of map locations corresponding to an electrical signal of a first set of electrical signals, the first set of map locations having a first spatial arrangement, wherein the first set of electrical signals comprises a first subset of the plurality of electrical signals; receive, from the input device, a user selection of a second selected portion of the cardiac map, the second selected portion comprising a second set of map locations, each of the second set of map locations corresponding to an electrical signal of a second set of electrical signals, the second set of map locations having a second spatial arrangement, wherein the second set of electrical signals comprises a second subset of the plurality of electrical signals; and facilitate display, via the display, of (1) a first set of electrical signal representations, each electrical signal representation of the first set of electrical signal representations corresponding to one electrical signal of the first set of electrical signals, the first set of electrical signal representations comprising a third spatial arrangement, wherein the third spatial arrangement corresponds to the first spatial arrangement; and (2) a second set of electrical signal representations, each electrical signal representation of the second set of electrical signal representations corresponding to one electrical signal of the second set of electrical signals, the second set of electrical signal representations comprising a fourth spatial arrangement, wherein the fourth spatial arrangement corresponds to the second spatial arrangement.

In an Example 35, the system of Example 34, wherein the first set of electrical signal representations is displayed in a first column and the second set of electrical signal representations is displayed in a second column, and wherein the second column is displayed adjacent the first column.

While MULTIPLE embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; impre-cise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

Embodiments of systems and methods described herein facilitate processing sensed cardiac electrical signals to present, via a graphical user interface (GUI), representations of electrical signals associated with an electroanatomical map. In embodiments, representations of electrical signals (e.g., electrograms) may facilitate providing detailed information about user-selected portions of the electroanatomical map in a manner that facilitates preserving the spatial (with respect to the displayed map) relationship between the electrical signals. That is, for example, a set of electrical signal representations (e.g., electrogram representations) may be presented in one or more columns adjacent a cardiac map. The spatial arrangement of the set of electrical signal representations may be configured to correspond to a spatial representation of map locations corresponding to the electrical signals represented by the electrical signal representations.

According to embodiments, to perform aspects of embodiments of the methods described herein, cardiac electrical signals may be obtained from a mapping catheter (e.g., associated with a mapping system), a recording system, a coronary sinus (CS) catheter or other reference catheter, an ablation catheter, a memory device (e.g., a local memory, a cloud server, etc.), a communication component, a medical device (e.g., an implantable medical device, an external medical device, a telemetry device, etc.), and/or the like.

Figure 1:
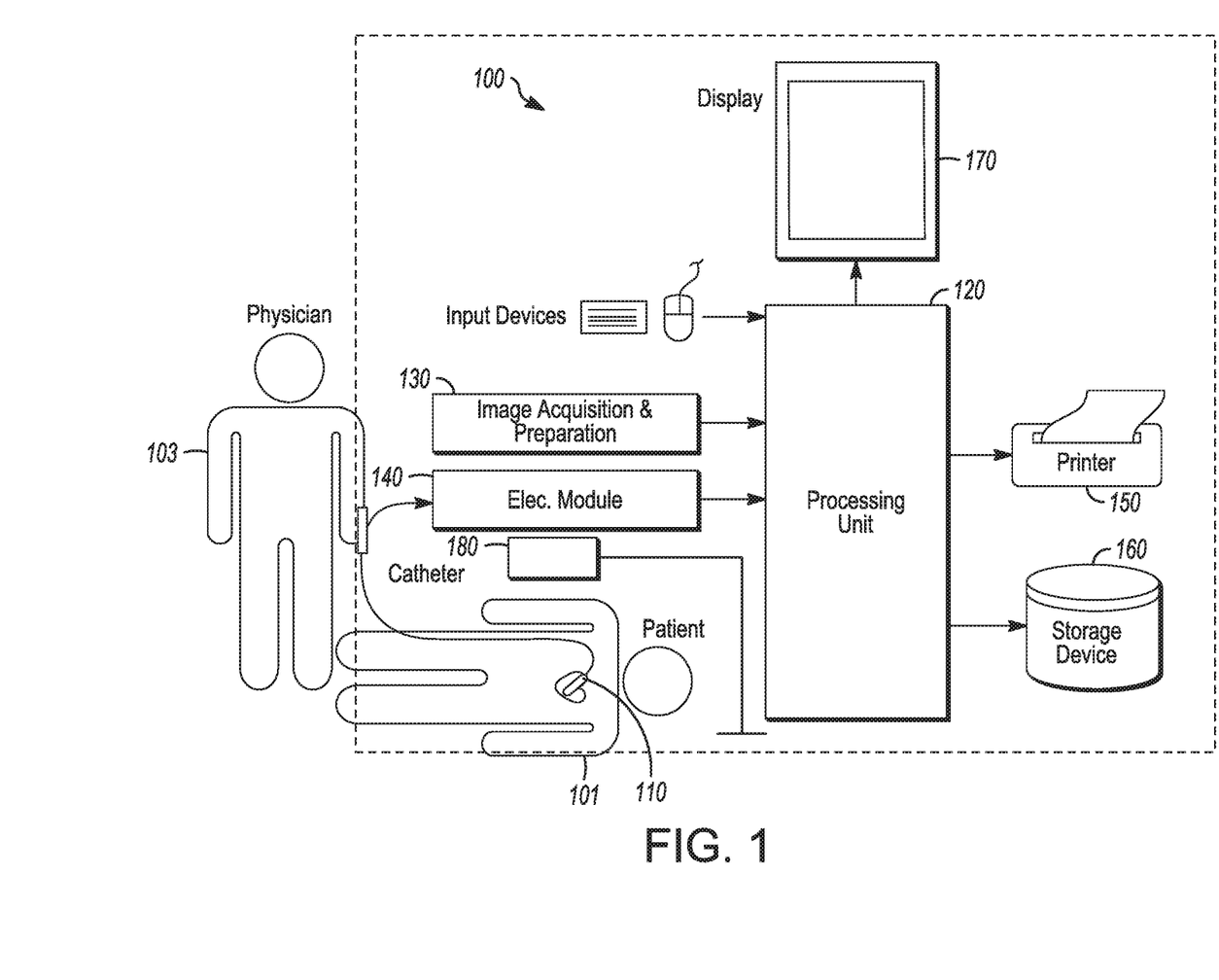
FIG. 1 is a conceptual schematic diagram depicting an illustrative cardiac mapping system, in accordance with embodiments of the subject matter disclosed herein.

As the term is used herein, a sensed cardiac electrical signal may refer to one or more sensed signals. Each cardiac electrical signal may include a number of intracardiac electrograms (EGMs) sensed within a patient's heart, and may include any number of features that may be ascertained by aspects of the system 100. Examples of cardiac electrical signal features include, but are not limited to, activation times, activations, activation waveforms, filtered activation waveforms, minimum voltage values, maximum voltages values, maximum negative time-derivatives of voltages, instantaneous potentials, voltage amplitudes, dominant frequencies, peak-to-peak voltages, and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

Each cardiac signal also may be associated with a set of respective position coordinates that corresponds to the location at which the cardiac electrical signal was sensed. Each of the respective position coordinates for the sensed cardiac signals may include three-dimensional Cartesian coordinates, polar coordinates, and/or the like. In embodiments, other coordinate systems can be used. In embodiments, an arbitrary origin is used and the respective position coordinates refer to positions in space relative to the arbitrary origin. Since, in embodiments, the cardiac signals may be sensed on the cardiac surfaces, the respective position coordinates may be on the endocardial surface, epicardial surface, in the mid-myocardium of the patient's heart, and/or in the vicinity of one of one of these.

FIG. 1 shows a schematic diagram of an exemplary embodiment of a cardiac mapping system 100. As indicated above, embodiments of the subject matter disclosed herein may be implemented in a mapping system (e.g., the mapping system 100), while other embodiments may be implemented in an ablation system, a recording system, a computer analysis system, and/or the like. The mapping system 100 includes a moveable catheter 110 having MULTIPLE spatially distributed electrodes. During a signal-acquisition stage of a cardiac mapping procedure, the catheter 110 is displaced to MULTIPLE locations within the heart chamber into which the catheter 110 is inserted. In some embodiments the distal end of the catheter 110 is fitted with MULTIPLE electrodes spread somewhat uniformly over the catheter. For example, the electrodes may be mounted on the catheter 110 following a 3D olive shape, a basket shape, and/or the like. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, shape memory material such as Nitinol, actuable hinged structure, and/or the like. According to embodiments, the catheter 110 may be a mapping catheter, an ablation catheter, a diagnostic catheter, a CS catheter, and/or the like. For example, aspects of embodiments of the catheter 110, the electrical signals obtained using the catheter 110, and subsequent processing of the electrical signals, as described herein, may also be applicable in implementations having a recording system, ablation system, and/or any other system having a catheter with electrodes that may be configured to obtain cardiac electrical signals.

At each of the locations to which the catheter 110 is moved, the catheter's MULTIPLE electrodes acquire signals resulting from the electrical activity in the heart. Consequently, reconstructing and presenting to a user (such as a doctor and/or technician) physiological data pertaining to the heart's electrical activity may be based on information acquired at MULTIPLE locations, thereby providing a more accurate and faithful reconstruction of physiological behavior of the endocardium surface. The acquisition of signals at MULTIPLE catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on MULTIPLE measurements over several heart beats, the measurements may be synchronized with one another so that the measurement are performed at approximately the same phase of the heart cycle. The signal measurements over MULTIPLE beats may be synchronized based on features detected from physiological data such as surface electrocardiograms (ECGs) and/or intracardiac electrograms (EGMs).

The cardiac mapping system 100 further includes a processing unit 120 which performs several of the operations pertaining to the mapping procedure, including the reconstruction procedure to determine the physiological information at the endocardium surface (e.g., as described above) and/or within a heart chamber. The processing unit 120 also may perform a catheter registration procedure. The processing unit 120 also may generate a 3D grid used to aggregate the information captured by the catheter 110 and to facilitate display of portions of that information.

The location of the catheter 110 inserted into the heart chamber can be determined using a conventional sensing and tracking system 180 that provides the 3D spatial coordinates of the catheter and/or its MULTIPLE electrodes with respect to the catheter's coordinate system as established by the sensing and tracking system. These 3D spatial locations may be used in building the 3D grid. Embodiments of the system 100 may use a hybrid location technology that combines impedance location with magnetic location technology. This combination may enable the system 100 to accurately track catheters that are connected to the system 100. Magnetic location technology uses magnetic fields generated by a localization generator positioned under the patient table to track catheters with magnetic sensors. Impedance location technology may be used to track catheters that may not be equipped with a magnetic location sensor, and may utilize surface ECG patches.

In embodiments, to perform a mapping procedure and reconstruct physiological information on the endocardium surface, the processing unit 120 may align the coordinate system of the catheter 110 with the endocardium surface's coordinate system. The processing unit 110 (or some other processing component of the system 100) may determine a coordinate system transformation function that transforms the 3D spatial coordinates of the catheter's locations into coordinates expressed in terms of the endocardium surface's coordinate system, and/or vice-versa. In embodiments, such a transformation may not be necessary, as embodiments of the 3D grid described herein may be used to capture contact and non-contact EGMs, and select mapping values based on statistical distributions associated with nodes of the 3D grid. The processing unit 120 also may perform post-processing operations on the physiological information to extract and display useful features of the information to the operator of the system 100 and/or other persons (e.g., a physician).

According to embodiments, the signals acquired by the MULTIPLE electrodes of catheter 110 are passed to the processing unit 120 via an electrical module 140, which may include, for example, a signal conditioning component. The electrical module 140 may be configured to receive the signals communicated from the catheter 110 and perform signal enhancement operations on the signals before they are forwarded to the processing unit 120. The electrical module 140 may include signal conditioning hardware, software, and/or firmware that may be used to amplify, filter and/or sample intracardiac potential measured by one or more electrodes. The intracardiac signals typically have a maximum amplitude of 60 mV, with a mean of a few millivolts.

In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal may be filtered to remove the frequency corresponding to the power supply (e.g., 60 Hz). Other types of signal processing operations such as spectral equalization, automatic gain control, etc. may also take place. For example, in embodiments, the intracardiac signals may be unipolar signals, measured relative to a reference (which may be a virtual reference) such as, for example, a coronary sinus catheter or Wilson's Central Terminal (WCT), from which the signal processing operations may compute differences to generate multipolar signals (e.g., bipolar signals, tripolar signals, etc.). The signals may be otherwise processed (e.g., filtered, sampled, etc.) before and/or after generating the multipolar signals. The resultant processed signals are forwarded by the module 140 to the processing unit 120 for further processing.

In embodiments, the processing unit 120 may be configured to process the resultant processed signals. In embodiments, because the processing unit 120 may be configured to process any number of different types of electrical signals, whether they have been preprocessed or not, the terms "electrical signal(s)," "cardiac electrical signal(s)" and terms including one or more of the aforementioned, shall be understood to refer to electrical signals, processed (e.g., "pre-processed") electrical signals, raw signal data, interpolated electrical signals, estimated electrical signals, and/or any other type of information representing an electrical signal, as described herein. In embodiments, the processing unit 120 may be configured to facilitate processing sensed cardiac electrical signals to present, via a GUI, representations of electrical signals associated with a cardiac map. In embodiments, representations of electrical signals (e.g., electrograms) may facilitate providing detailed information about user-selected portions of the cardiac map in a manner that facilitates preserving the spatial (with respect to the displayed map) relationship between the electrical signals.

Embodiments of the processing unit 120 may be configured to receive a number of electrical signals such as, for example, cardiac electrical signals (e.g., electrograms). The processing unit 120 may receive the electrical signals from the electrical module 140, from a memory device, from a catheter (e.g., the catheter 110), from another computing device, from a user via a user input device, and/or the like.

In embodiments, the processing unit 120 may receive an indication of a measurement location corresponding to each electrical signal. The processing unit 120 may be configured to generate, based on the electrical signals, a cardiac map, which may be presented via a display device 170. In embodiments, the cardiac map includes a number of annotations representing a number of cardiac signal features, which may include, for example, one or more activation times, minimum voltage values, maximum voltage values, maximum negative time-derivatives of voltage, instantaneous potentials, voltage amplitudes, dominant frequencies, and/or peak-to-peak voltages.

The processing unit 120 may be further configured to receive, from an input device, a user selection of a selected portion of the cardiac map; identify a set of map locations corresponding to the selected portion; and identify, for each of the set of map locations, a corresponding electrical signal of a set of electrical signals. The processing unit 120 may identify the map locations and/or the corresponding electrical signals based on user input, one or more algorithms, and/or the like. For example, in embodiments, the selected portion of the map may include a discrete set of selected map location representations (e.g., each of which may represent one or more electrograms or other parameters such as, for example, cardiac signal features, aggregated electrical signals, etc.) presented on the cardiac map. The set of corresponding electrical signals may include one or more electrical signals corresponding to each selected map location representation. In embodiments, the selected portion of the map may include a curve and/or grid intersecting a number of map location representations, where each corresponding electrical signal corresponds to one of the map location representations intersected by the curve. In embodiments, the corresponding electrical signals may be identified by identifying an electrical signal most closely associated (spatially) to a map location representation, a part of a selected portion, and/or the like. Any number of different algorithms, selection processes, and/or the like may be implemented for identifying map locations and/or corresponding electrical signals.

The set of electrical signals may include a subset (e.g., one or more of) the received electrical signals. The set of map locations may include a first spatial arrangement, and the processing unit 120 may be configured to facilitate display, via the display device, of a set of electrical signal representations, each electrical signal representation of the set of electrical signal representations corresponding to one of the set of electrical signals. The set of electrical signal representations may include a second spatial arrangement, where the second spatial arrangement corresponds to the first spatial arrangement.

In embodiments, the processing unit 120 may be further configured to: receive, via the input device, a user selection of an additional selected portion of the cardiac map; determine, based on the user input, an additional selected portion of the cardiac map, the additional selected portion comprising an additional set of map locations, each of the additional set of map locations corresponding to an electrical signal of an additional set of electrical signals. The additional set of map locations may include a third spatial arrangement, and the processing unit 120 may be configured to facilitate display, via the display, of an additional set of electrical signal representations simultaneously with the display of the set of electrical signal representations. In embodiments, each electrical signal representation of the additional set of electrical signal representations corresponding to one of the electrical signal set of electrical signals, the additional set of electrical signal representations having a fourth spatial arrangement, where the fourth spatial arrangement corresponds to the third spatial arrangement. According to embodiments, the set of electrical signal representations may be displayed in a first column and the additional set of electrical signal representations may be displayed in a second column, and the second column may be displayed adjacent the first column.

In embodiments, for example, a user may select a portion of the cardiac map by drawing, with an input device configured to interact with a GUI element (e.g., a cursor, virtual probe, etc.), a curve. A processing unit may be configured to receive the user selection of the selected portion of the cardiac map, to identify a set of map locations corresponding to the selected portion, and to identify, for each of the set of map locations, a corresponding electrical signal of a set of electrical signals. The processing unit may determine a spatial arrangement of the set of map locations, and may facilitate presentation of electrical signal representations having a spatial arrangement that corresponds to the spatial arrangement of the set of map locations. That is, for example, the electrical signal representations may be displayed in a column adjacent the cardiac map, and the vertical spacing between each pair of adjacent electrical signal representations may be proportional to the vertical component of the spacing between the corresponding map locations. In embodiments, MULTIPLE columns of electrical signal representations may be presented, corresponding to MULTIPLE selected portions of the cardiac map (e.g., MULTIPLE curves drawn on the cardiac map).

According to embodiments, the processing unit may be configured to present an interactive grid, superimposed over a portion of the cardiac map, where the portion of the cardiac map falling within the grid is the selected portion of the cardiac map. In this manner, a user may change the selected portion of the cardiac map by moving and/or re-sizing the grid. In embodiments, the user may move and/or resize the grid using a user input device configured to facilitate manipulation of the grid and/or other GUI elements. MULTIPLE columns of electrical signal representations may be presented adjacent the cardiac map, each of the columns corresponding to one of the columns of the grid. The processing unit may be configured to identify one or more map locations corresponding to each cell of the grid, and, for each map location, identify a corresponding electrical signal of a set of electrical signals. The processing unit may determine a spatial arrangement of the set of map locations, and may facilitate presentation of electrical signal representations having a spatial arrangement that corresponds to the spatial arrangement of the set of map locations. That is, for example, the electrical signal representations may be displayed in one or more columns adjacent the cardiac map, each column corresponding to a column of the grid. The vertical spacing between each pair of adjacent electrical signal representations may be proportional to the vertical component of the spacing between the corresponding map locations.

As further shown in FIG. 1, the cardiac mapping system 100 also may include peripheral devices such as a printer 150 and/or display device 170, both of which may be interconnected to the processing unit 120. Additionally, the mapping system 100 includes storage device 160 that may be used to store data acquired by the various interconnected modules, including the volumetric images, raw data measured by electrodes and/or the resultant endocardium representation computed therefrom, the partially computed transformations used to expedite the mapping procedures, the reconstructed physiological information corresponding to the endocardium surface, and/or the like.

In embodiments, the processing unit 120 may be configured to automatically improve the accuracy of its algorithms by using one or more artificial intelligence (i.e., machine-learning) techniques, classifiers, and/or the like. In embodiments, for example, the processing unit may use one or more supervised and/or unsupervised techniques such as, for example, support vector machines (SVMs), k-nearest neighbor techniques, artificial neural networks, and/or the like. In embodiments, classifiers may be trained and/or adapted using feedback information from a user, other metrics, and/or the like.

The illustrative cardiac mapping system 100 shown in FIG. 1 is not intended to suggest any limitation as to the scope of use or functionality of embodiments of the present disclosure. Neither should the illustrative cardiac mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein. For example, the electrical module 140 may be integrated with the processing unit 120. Additionally, or alternatively, aspects of embodiments of the cardiac mapping system 100 may be implemented in a computer analysis system configured to receive cardiac electrical signals and/or other information from a memory device (e.g., a cloud server, a mapping system memory, etc.), and perform aspects of embodiments of the methods described herein for processing cardiac information (e.g., determining annotation waveforms, etc.). That is, for example, a computer analysis system may include a processing unit 120, but not a mapping catheter.

Figure 2:
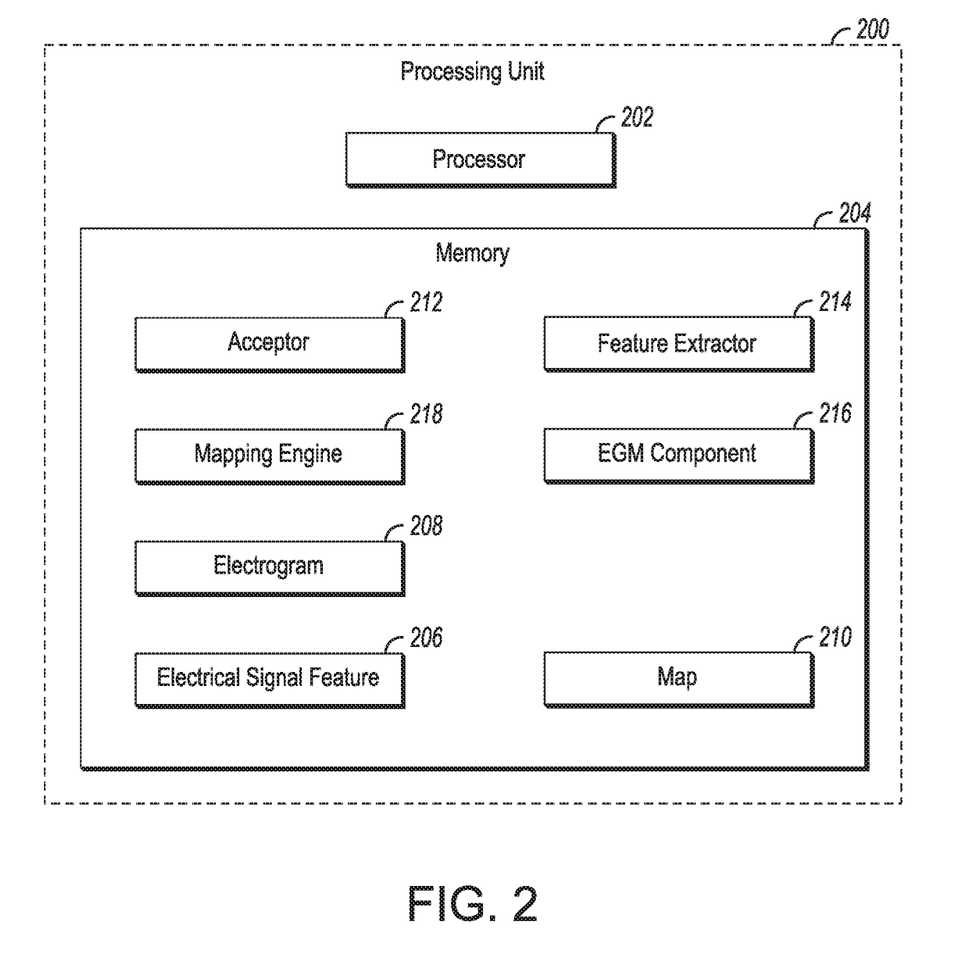
FIG. 2 is a block diagram depicting an illustrative processing unit, in accordance with embodiments of the subject matter disclosed herein.

FIG. 2 is a block diagram of an illustrative processing unit 200, in accordance with embodiments of the disclosure. The processing unit 200 may be, be similar to, include, or be included in the processing unit 120 depicted in FIG. 1. As shown in FIG. 2, the processing unit 200 may be implemented on a computing device that includes a processor 202 and a memory 204. Although the processing unit 200 is referred to herein in the singular, the processing unit 200 may be implemented in MULTIPLE instances (e.g., as a server cluster), distributed across MULTIPLE computing devices, instantiated within MULTIPLE virtual machines, and/or the like. One or more components for facilitating cardiac mapping may be stored in the memory 204. In embodiments, the processor 202 may be configured to instantiate the one or more components to process electrical signals received from electrodes, extract one or more electrical signal features 206 from one or more electrograms 208, and to generate one or more cardiac maps 210, either of which may be stored in the memory 204.

As is further depicted in FIG. 2, the processing unit 200 may include an acceptor 212 configured to receive electrical signals. The acceptor 212 may be configured to receive electrical signals from a mapping catheter (e.g., the mapping catheter 110 depicted in FIG. 1), a memory device (e.g., the memory 204), a server, and/or the like. The measured electrical signals may include a number of intracardiac electrograms (EGMs) sensed within a patient's heart. The acceptor 212 may also receive an indication of a measurement location corresponding to each of the electrical signals. In embodiments, the acceptor 212 may be configured to determine whether to accept the electrical signals that have been received. The acceptor 212 may utilize any number of different components and/or techniques to determine which electrical signals or beats to accept, such as filtering, beat matching, morphology analysis, positional information (e.g., catheter motion), respiration gating, and/or the like.

The accepted electrical signals are received by a feature extractor 214 that is configured to extract at least one electrical signal feature from each of the electrical signals. In embodiments, an extracted electrical signal feature may be used to annotate a cardiac map, in which case, the extracted electrical signal feature may be referred to, interchangeably, as an annotation feature. In embodiments in which the electrical signal is a cardiac electrical signal, an extracted signal feature may be referred to, interchangeably, as a cardiac electrical signal feature. In embodiments, the at least one electrical signal feature includes at least one value corresponding to at least one annotation metric. The at least one feature may include at least one event, where the at least one event includes the at least one value corresponding to the at least one metric and/or at least one corresponding time (a corresponding time does not necessarily exist for each annotation feature). According to embodiments, the at least one electrical signal feature may include, for example, an activation time, detected activation (e.g., a component of an activation waveform), activation waveform, activation histogram, minimum voltage value, maximum voltage value, maximum negative time-derivative of voltage, an instantaneous potential, a voltage amplitude, a dominant frequency, a peak-to-peak voltage, an activation duration, an annotation waveform (e.g., an activation waveform), and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

As shown in FIG. 2, the processing unit 200 includes an electrogram (EGM) component 216. According to embodiments, the EGM component 216 is configured to facilitate displaying electrograms corresponding to a selected portion of a cardiac map. According to embodiments, a "selected portion" of a cardiac map is a portion of a cardiac map that has been designated as such, such as, for example, via user input, an automatic algorithm, and/or the like. In embodiments, for example, a user (e.g., a clinician) interacts with a graphical user interface (GUI) via a user input device to select a portion of a cardiac map. In embodiments, the GUI may facilitate selection of one or more electrical signal representations, curves along the surface of the cardiac map, regions of the cardiac map, and/or the like, via interaction with a GUI. In embodiments, the GUI may allow the user to interact with the cardiac map directly using a selection indicator (e.g., by utilizing a cursor, virtual probe, moveable grid, etc.) to select points and/or regions of the map, hover over points and/or regions of the map, and/or the like, to facilitate selection of a portion of the cardiac map. In embodiments, the EGM component 216 may be configured to automatically select a selected portion of a map in response to user input that is not directly related to selection of a portion of the cardiac map such as, for example, adjustments of mapping parameters, selection of a time period, selection of a type of cardiac signal feature and/or electrical signal, submitting a search query for electrical signals satisfying one or more criteria, and/or the like.

In embodiments, the EGM component 216 may be configured to identify a set of map locations corresponding to the selected portion and, for each of the set of map locations, identify a corresponding electrical signal of a set of electrical signals. The EGM component 216 may be further configured to determine a spatial arrangement of the set of map locations (which may be identified, to a user, via map location representations). The EGM component 216 may be configured to present representations of the corresponding electrical signals in a manner in which the spatial context of the map locations with respect to one another is reflected. That is, for example, embodiments of the EGM component 216 may be configured to facilitate display, via a display device, of a set of electrical signal representations, each electrical signal representation of the set of electrical signal representations corresponding to one of the set of electrical signals, where the set of electrical signal representations may include a spatial arrangement that corresponds to the spatial arrangement of the map locations corresponding to the selected portion of the cardiac map. The spatial arrangement of the electrical signal representations may be determined using any number of different techniques. For example, in embodiments, the EGM component 216 may be configured to determine the spatial arrangement of the electrical signal representations by performing a linear scaling operation based on the spatial arrangement of the corresponding map locations.

Additionally, the processing unit 200 includes a mapping engine 216 that is configured to facilitate presentation of a map 208 corresponding to a cardiac surface based on the electrical signals. In embodiments, the map 208 may include a voltage map, an activation map, a fractionation map, velocity map, confidence map, and/or the like. In embodiments, the mapping engine 216 may be, include, be similar to, be included within, and/or be otherwise integrated with the EGM component 214. In embodiments, the mapping engine 216 may be configured to facilitate display, via the display device, of the cardiac map and representations of electrical signals. As shown, for example, a representation of an electrical signal may include a waveform (e.g., a curve representing voltage over time). In embodiments, more than one representation of an electrical signal may be presented on the GUI.

Figure 3A:
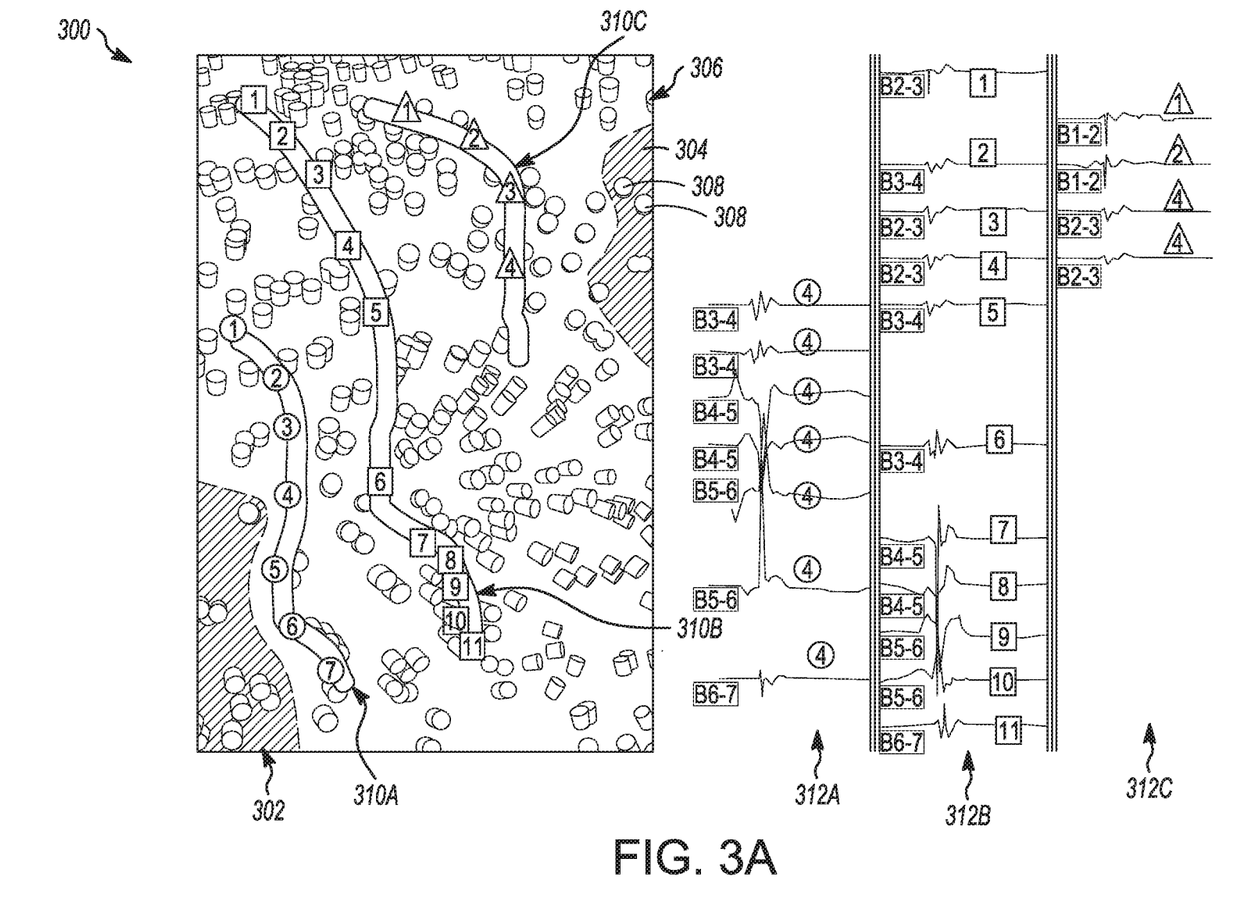
FIGS. 3A and 3B depict illustrative cardiac maps, in accordance with embodiments of the subject matter disclosed herein.

FIG. 3A depicts an illustrative screenshot from an interactive graphical user interface (GUI) 300 presented using a display device associated with a cardiac mapping system, showing an illustrative portion of a cardiac map 302, in accordance with embodiments of the subject matter disclosed herein. According to embodiments, the cardiac mapping system may be, be similar to, include similar features as, include, or be included within the mapping system 100 depicted in FIG. 1. In embodiments, the GUI 300 may be configured to present only one view of the cardiac map 302 at a time. In embodiments, the GUI 300 may be configured to present, simultaneously, sequentially, and/or alternatively, any number of different views of any number of cardiac maps. In embodiments, for example, the GUI 300 may be configured to present a first cardiac map having annotations representing activations and a second cardiac map having annotations representing electrical potential, current density, and/or the like.

As shown in FIG. 3A, the cardiac map 302 includes an anatomical shell 304 and annotations 306 displayed on the anatomical shell 304. In embodiments, the map may be an activation map, on which activation locations are indicated by raised bumps (map location representations) 308. In embodiments, raised bumps 308 (or other displayed features) may be used to indicate any number of different metrics, values, events, and/or the like. In embodiments, annotations (e.g., electrical signal features, quantities corresponding to—e.g., derived from—electrical signal features) may be represented using any number of different colors, presented using any number of different types of gradient patterns. In embodiments, in addition to, or in lieu of, colors, other representations may be used to represent cardiac signal features such as, for example, textures, location markers, curves, vectors, and/or the like. In embodiments, the raised bumps 308 may be configured to represent a location associated with an acquired electrical signal (e.g., an EGM), a virtual location associated with an aggregation of acquired electrical signals, and/or the like. In embodiments, the GUI may also include a legend (not shown) configured to indicate the values represented by the annotation colors.

In embodiments, the background of the map 302 may include a gradient color pattern 304 indicative of cardiac signal features (e.g., voltage and/or activation patterns). The cardiac map 302 includes map location representations 308, which, in the illustrated embodiments, are raised bumps on the map 302. In embodiments, the map location representations may represent map location points where electrogram data has been recorded. According to embodiments, for example, the GUI may be configured to receive, from a user input device, a selection of a selected portion of the cardiac map 302. The user input device used to make the selection may include a mouse, a touchscreen and/or the like, that is used to manipulate a selection tool that is provided on the GUI provided by the display device. The selection tool may include, for example, a brush, a cursor for enclosing the selected portion by drawing a freeform shape around the selected portion, an expandable polygon selection tool, a virtual probe, and/or the like, and may be, in embodiments, selected from a number of optional selection tools. In embodiments, the selection tool may have an adjustable size, behavior and/or other characteristics thereof. In this manner, for example, a user may select a desired selection tool and a size thereof. Selecting a selected portion of the map 302 may include, for example, drawing a curve, moving and/or re-sizing a grid, circling the selected portion of the map using a mouse or touchscreen device to manipulate a cursor, brushing over the selected portion of the map using an input device to manipulate a brush, and/or the like. According to embodiments, one or more portions of a map may be interactive such that a user may position a mouse cursor over a portion of the map, and interact with that portion (e.g., by clicking a right mouse button) to reveal additional information and/or functionality.

As shown in the example of FIG. 3A, a user has drawn three curves 310A, 310B, and 310C on the surface of the cardiac map 302. Along each curve, map locations (and, thus, corresponding electrical signals) are selected by a processing unit based on user-defined and/or algorithmic criteria. As shown in FIG. 3A, a set of columns of electrical signal representations are presented adjacent the cardiac map 302. A first set 312A of electrical signal representations corresponds to the first curve 310A, a second set 312B of electrical signal representations corresponds to the second curve 310B, and a third set 312C of electrical signal representations corresponds to the third curve 310C. As shown, the spatial arrangement of each set of electrical signal representations corresponds (e.g., is geometrically proportional, in one or more respects,) to the spatial arrangement of the corresponding set of map location representations. That is, for example, each pair (e.g., (1,2), (2,3), (3,4), etc.) of adjacent electrical signal representations of the first set 312A of electrical signal representations has a vertical spacing that corresponds to the vertical component of the spacing of the corresponding adjacent map locations (e.g., (1,2), (2,3), (3,4), etc.). In embodiments, the user may adjust the curves (selection indicators), which may automatically and dynamically result in identification of a new set of map locations and corresponding electrical signals, which may facilitate dynamic display of corresponding electrical signal representations.

Figure 3B:
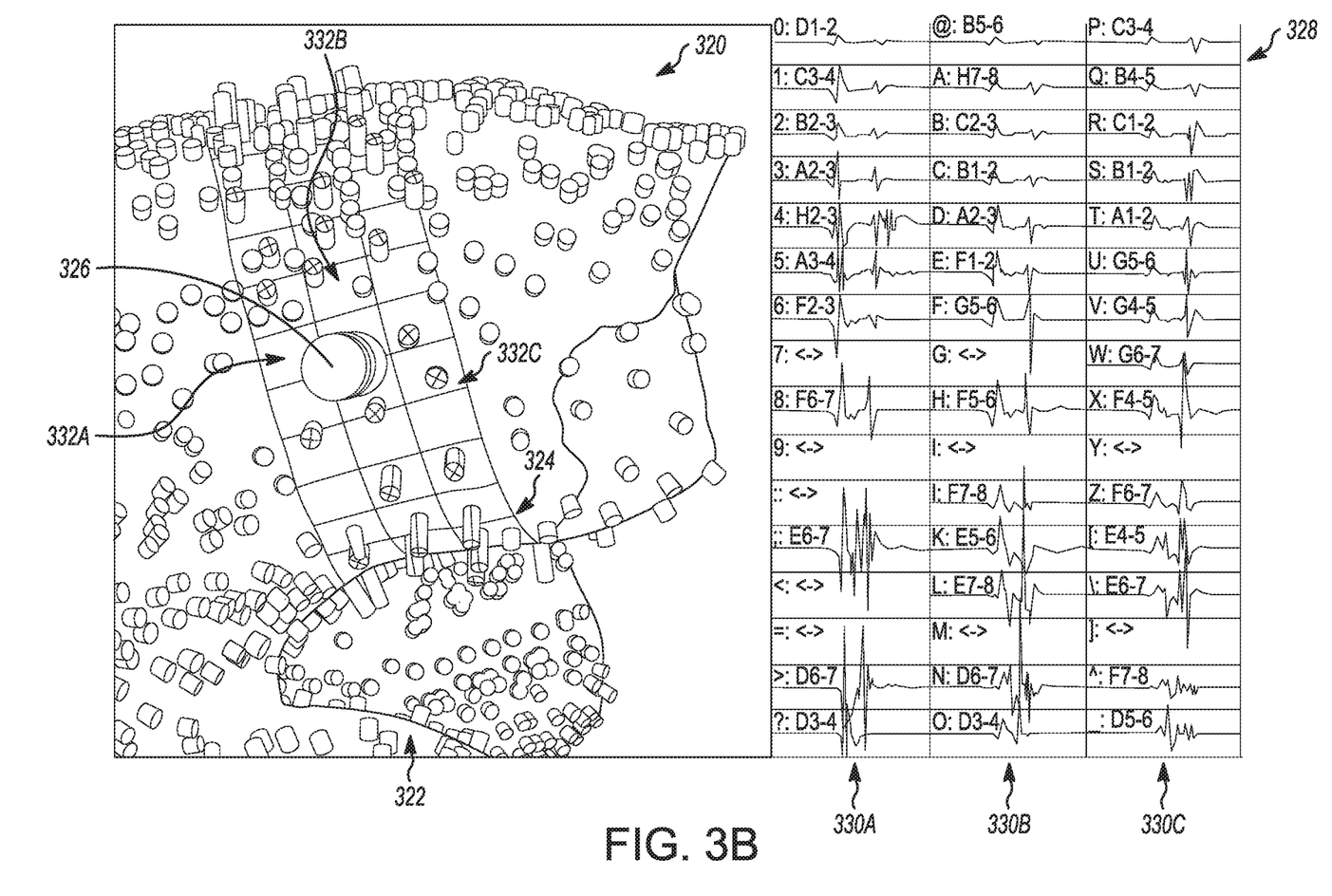

Another tool for selecting electrodes may include a grid on the surface of the cardiac map, where each cell in the grid corresponds to a cell in a set of corresponding electrical signal representations that may be displayed in a grid arrangement. FIG. 3B an illustrative screenshot from an interactive GUI 320, showing another illustrative portion of a cardiac map 322, in accordance with embodiments of the subject matter disclosed herein. According to embodiments, the cardiac map 322 may be, or include, one or more selectable GUI elements such that, for example, a user can move a cursor over a portion of the cardiac map 322 and select the portion of the cardiac map 322 to which the cursor points, for example, by pressing a mouse button, tapping a touchscreen, and/or the like. In embodiments, the GUI 320 may be, be similar to, include, or be included in the GUI 300 of FIG. 3A, except that the selection indicator 324 comprises an interactive grid that can be moved and/or resized by a user to select a selected portion of the cardiac map 322. As shown in FIG. 3B, the selection indicator 324 may include a virtual probe 326 (or "handle") that can be grabbed, using a GUI element manipulated via an input device, to move and/or re-size the grid 324. In embodiments, the grid 324 may be interacted with directly using a GUI element.

As shown in FIG. 3B, a set 328 of electrical signal representations (arranged according to a grid) having a set of columns 330A, 330B, and 330C of electrical signal representations is presented adjacent the cardiac map 322. The first column 330A of electrical signal representations corresponds to the first column 332A of the selection indicator grid 324, the second column 330B of electrical signal representations corresponds to the second column 332B of the selection indicator grid 324, and the third column 330C of electrical signal representations corresponds to the third column 332C of the selection indicator grid 324. As shown, the spatial arrangement of the set 328 of electrical signal representations corresponds (e.g., is geometrically proportional, in one or more respects,) to the spatial arrangement of the corresponding set of map location representations. That is, for example, each pair of adjacent electrical signal representations of the first column 330A of electrical signal representations has a vertical spacing that corresponds to the vertical component of the spacing of the corresponding adjacent map locations. In embodiments, the grid orientation, size, location, and/or cell spacing can be dynamically adjusted in the GUI. The displayed electrical signal representations 328 may be dynamically adjusted as the grid is manipulated. The selection indicator grid 324 (and, correspondingly, the set 328 of electrical signal representations) may include any number of columns and/or rows.

The illustrative processing unit 200 shown in FIG. 2 and the illustrative GUIs 300 and 320 are not intended to suggest any limitation as to the scope of use or functionality of embodiments of the present disclosure. Neither should the illustrative processing unit 200 and/or the GUIs 300 and 320 be interpreted as having any dependency or requirement related to any single component or combination of components illustrated therein. Additionally, any one or more of the components and/or features depicted in FIGS. 2, 3A, and 3B may be, in embodiments, integrated with various ones of the other components and/or features depicted therein (and/or components not illustrated), all of which are considered to be within the ambit of the subject matter disclosed herein.

The processing unit 200 may (alone and/or in combination with other components of the system 100 depicted in FIG. 1, and/or other components not illustrated) perform any number of different functions and/or processes associated with cardiac mapping (e.g., triggering, blanking, field mapping, etc.) such as, for example, those described in U.S. Pat. No. 8,428,700, entitled "ELECTROANATOMICAL MAPPING;" U.S. Pat. No. 8,948,837, entitled "ELECTROANATOMICAL MAPPING;" U.S. Pat. No. 8,615,287, entitled "CATHETER TRACKING AND ENDOCARDIUM REPRESENTATION GENERATION;" U.S. Patent Publication 2015/0065836, entitled "ESTIMATING THE PREVALENCE OF ACTIVATION PATTERNS IN DATA SEGMENTS DURING ELECTROPHYSIOLOGY MAPPING;" U.S. Pat. No. 6,070,094, entitled "SYSTEMS AND METHODS FOR GUIDING MOVABLE ELECTRODE ELEMENTS WITHIN MULTIPLE-ELECTRODE STRUCTURE;" U.S. Pat. No. 6,233,491, entitled "CARDIAC MAPPING AND ABLATION SYSTEMS;" U.S. Pat. No. 6,735,465, entitled "SYSTEMS AND PROCESSES FOR REFINING A REGISTERED MAP OF A BODY CAVITY;" the disclosures of which are hereby expressly incorporated herein by reference.

According to embodiments, various components of the mapping system 100, illustrated in FIG. 1, and/or the processing unit 200, illustrated in FIG. 2, may be implemented on one or more computing devices. A computing device may include any type of computing device suitable for implementing embodiments of the disclosure. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2 with reference to various components of the system 100 and/or processing unit 200.

In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, memory (e.g., the storage device 160 depicted in FIG. 1, and/or the memory 204 depicted in FIG. 2) includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 160 and/or 204 stores computer-executable instructions for causing a processor (e.g., the processing unit 120 depicted in FIG. 1 and/or the processor 202 depicted in FIG. 2) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Examples of such program components include the electrical signal (electrogram 208), electrical signal feature 206, the map 210, the acceptor 212, the feature extractor 214, the EGM component 216, and/or the mapping engine 218. Program components may be programmed using any number of different programming environments, including various languages, development kits, frameworks, and/or the like. Some or all of the functionality contemplated herein may also, or alternatively, be implemented in hardware and/or firmware.

Figure 4:
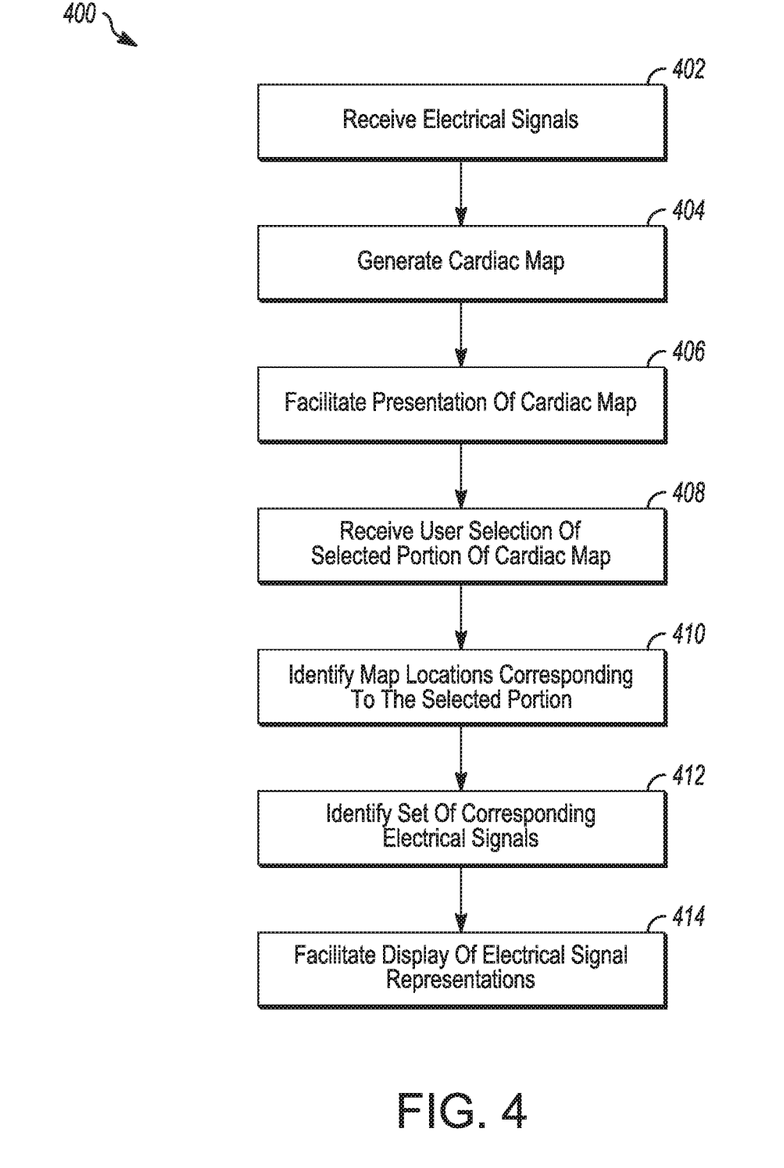
FIG. 4 is a flow diagram depicting an illustrative method for presenting cardiac information, in accordance with embodiments of the subject matter disclosed herein.

FIG. 4 is a flow diagram depicting an illustrative method 400 of presenting cardiac information, in accordance with embodiments of the disclosure. Aspects of embodiments of the method 400 may be performed, for example, by a processing unit (e.g., the processing unit 120 depicted in FIG. 1, and/or the processing unit 200 depicted in FIG. 2). Embodiments of the method 400 include receiving a plurality of electrical signals (block 402). The electrical signals may be received from a catheter, a memory device, a computing device, and/or the like. Each of the electrical signals may be, include, be similar to, or be included in an electrogram. The catheter may be any catheter having one or more electrodes configured to obtain electrical signals (e.g., the mapping catheter 110 depicted in FIG. 1, a CS catheter, an ablation catheter, etc.). The processing unit also may receive an indication of a measurement location corresponding to each of the electrical signals. In embodiments, the processing unit and/or other components (e.g., the electrical module 140 depicted in FIG. 1) may be configured to determine whether to accept particular electrical signals (e.g., beats) based on one or more beat acceptance criteria.

According to embodiments, cardiac electric signal features may be extracted from the cardiac electrical signals (e.g., EGMs). Examples of features of the cardiac electrical signals include, but are not limited to, activation times, minimum voltage values, maximum voltages values, maximum negative time-derivatives of voltages, instantaneous potentials, voltage amplitudes, dominant frequencies, peak-to-peak voltages, and/or the like. Each of the respective points at which a cardiac electrical signal is sensed may have a corresponding set of three-dimensional position coordinates. For example, the position coordinates of the points may be represented in Cartesian coordinates. Other coordinate systems can be used, as well. In embodiments, an arbitrary origin is used and the respective position coordinates are defined with respect to the arbitrary origin. In some embodiments, the points have non-uniform spacing, while in other embodiments, the points have uniform spacing. In embodiments, the point corresponding to each sensed cardiac electrical signal may be located on the endocardial surface of the heart and/or below the endocardial surface of the heart.

As shown in FIG. 4, embodiments of the method 400 include generating, based on the electrical signals, a cardiac map (block 404). Embodiments of the method 400 further include facilitating presentation of a cardiac map on a display device (block 406). In embodiments, each of the received electrical signals may correspond to a cardiac map location (a location on the surface of the cardiac map). In embodiments, a cardiac map may be generated and/or annotated based, at least in part, on the cardiac electrical signal features. In embodiments, the cardiac map may also be generated and/or annotated, at least in part, using any number of other signals, techniques, and/or the like. For example, embodiments may utilize impedance mapping techniques to generate and/or annotate one or more portions of the cardiac map such as, for example, an anatomical shell upon which electrical signal features are represented. In embodiments, a surface may be fitted on one or more of the points associated with the cardiac electrical signals to generate a shell representing the endocardial surface of the one or more cardiac structures. In embodiments, a surface may also be fitted on one or more of the points associated with the cardiac electrical signals to generate a shell representing an epicardium surface or other excitable cardiac tissue. In embodiments, one or more of the cardiac electrical signal features at the corresponding points can be included on the shell to generate a cardiac map of the one or more cardiac structures. For example, embodiments may include displaying annotations on the cardiac map that represent features, extracted from the cardiac electrical signals and/or derived from other features, such as, for example, activation times, minimum voltage values, maximum voltages values, maximum negative time-derivatives of voltages, instantaneous potentials, voltage amplitudes, dominant frequencies, peak-to-peak voltages, and/or the like.

Cardiac electrical signal features may be represented on the cardiac map and may be, or include, any features extracted from one or more corresponding sensed cardiac electrical signals and/or derived from one or more of such features. For example, a cardiac electrical signal feature may be represented by a color, such that if the cardiac electrical signal feature has an amplitude or other value within a first range then the cardiac electrical signal feature may be represented by a first color, whereas if the cardiac electrical signal feature has an amplitude or other value that is within a second range that is different than the first range, the cardiac electrical may be represented by a second color. As another example, the cardiac electrical signal feature may be represented by a number (e.g., a 0.2 mV sensed cardiac electrical signal feature can be represented by a 0.2 at its respective position on the surface map). Examples of a cardiac electrical signal feature that can be represented at the first surface point include, but are not limited to, an activation, an activation time, an activation duration, an activation waveform, a filtered activation waveform, an activation waveform characteristic, a filtered activation waveform characteristic, a minimum voltage value, a maximum voltages value, a maximum negative time-derivative of voltage, an instantaneous potential, a voltage amplitude, a dominant frequency, a peak-to-peak voltage, and/or the like.

In embodiments, other features such as, for example, non-electrical signal features, non-cardiac electrical signal features, and/or the like, can be represented on an anatomical map at respective locations. Examples of non-electrical signal features include, but are not limited to, features derived from magnetic resonance imaging, a computerized tomography scan, ultrasonic imaging, and/or the like.

According to embodiments, a GUI used for presenting the map may include any number of different input tools for manipulating the map. For example, the GUI may include a play/pause button, a tool configured to facilitate manual selection of the histogram bin or bins, tools configured to facilitate manual adjustment of parameters (e.g., signal baseline definitions, thresholds, EGM characteristics, filters, etc.), and/or the like. In embodiments, for example, the GUI may include a selection tool that can facilitate refining selections of highlighted EGMs, select particular EGMs and/or activations, and/or the like.

As shown in FIG. 4, embodiments of the method 400 further include receiving, from an input device, a user selection of a selected portion of the cardiac map (block 408). The method includes identifying a set of map locations corresponding to the selected portion (block 410), and identifying, for each of the set of map locations, a corresponding electrical signal of a set of electrical signals (block 412). The set of map locations may include a first spatial arrangement, where the set of electrical signals includes a subset of the received electrical signals.

In embodiments, the method may also include facilitating display, via the display device, of a selection indicator, the selection indicator including a representation of the selected portion of the map. According to embodiments, the selected portion of the map may include at least one of (1) a curve, drawn using the input device, on the cardiac map; (2) a selected region of the cardiac map, and where the representation of the selected region includes a grid having a number of grid cells arranged in at least one column and at least one row, where each electrical signal of the set of electrical signals has a map location corresponding to one of the plurality of grid cells; and (3) a set of selected electrical signal representations, where the cardiac map includes a number of electrical signal representations, each of the electrical signal representations corresponding to one of the electrical signals.

The method 400 may also include facilitating display, via the display device, of a set of electrical signal representations (block 414), each electrical signal representation of the set of electrical signal representations corresponding to one of the set of electrical signals. In embodiments, the set of electrical signal representations may include a second spatial arrangement, where the second spatial arrangement corresponds to the first spatial arrangement. To display the set of electrical signal representations, the method 400 may include identifying, based on the selected portion of the cardiac map, the set of electrical signals; determining the first spatial arrangement; and determining, based on the first spatial arrangement, the second spatial arrangement. For example, in embodiments, the second spatial arrangement may be determined by performing a linear scaling operation based on the first spatial arrangement.

The illustrative method 400 shown in FIG. 4 is not intended to suggest any limitation as to the scope of use or functionality of embodiments of the present disclosure. Neither should the illustrative method 400 be interpreted as having any dependency nor requirement related to any single aspect or combination of aspects illustrated therein. Additionally, any one or more of the aspects depicted in FIG. 4 may be, in embodiments, integrated with various ones of the other aspects depicted therein (and/or components not illustrated), all of which are considered to be within the ambit of the present disclosure.

Various modifications and additions can be made to the exemplary embodiments discussed without departing from the scope of the presently disclosed subject matter. For example, while the embodiments described above refer to particular features, the scope of this disclosure also includes embodiments having different combinations of features and embodiments that do not include all of the described features. Accordingly, the scope of the subject matter disclosed herein is intended to embrace all such alternatives, modifications, and variations as fall within the scope of the claims, together with all equivalents thereof.

We claim:

1. A system for facilitating display of cardiac information, the system comprising:
a display device configured to present a cardiac map; and
a processing unit configured to:
receive a plurality of electrical signals sensed within a patient's heart;
generate, based on the plurality of electrical signals, the cardiac map;
facilitate display, via the display device, of the cardiac map, wherein each of the plurality of electrical signals corresponds to a cardiac map location;
receive, from an input device, a user selection of a selected portion of the cardiac map, the selected portion comprising a set of map locations, each of the set of map locations corresponding to an electrical signal of a set of electrical signals, the set of map locations having a first spatial arrangement, wherein the set of electrical signals comprises a subset of the plurality of electrical signals; and
facilitate display, via the display, of a set of electrical signal representations, each electrical signal representation of the set of electrical signal representations corresponding to one of the set of electrical signals, the set of electrical signal representations comprising a second spatial arrangement, wherein the second spatial arrangement corresponds to the first spatial arrangement, and wherein the second spatial arrangement is determined by performing a linear scaling operation based on the first spatial arrangement.

2. The system of claim 1, wherein each of the plurality of electrical signals comprises an electrogram.

3. The system of claim 1, wherein the processing unit is further configured to facilitate display, via the display device, of a selection indicator, the selection indicator comprising a representation of the selected portion of the map.

4. The system of claim 1, wherein the processing unit is further configured to:
identify, based on the selected portion of the cardiac map, the set of electrical signals;
determine the first spatial arrangement; and
determine, based on the first spatial arrangement, the second spatial arrangement.

5. The system of claim 1, wherein the selected portion of the map comprises a curve, drawn using the input device, on the cardiac map.

6. The system of claim 1, wherein the selected portion of the map comprises a selected region of the cardiac map, and wherein the representation of the selected region comprises a grid having a plurality of grid cells arranged in a plurality of columns and a plurality of rows.

7. The system of claim 6, wherein each electrical signal of the set of electrical signals has a map location corresponding to one of the plurality of grid cells.

8. The system of claim 1, wherein the processing unit is further configured to facilitate display, via the display device, of a plurality of electrical signal representations, each of the plurality of electrical signal representations corresponding to one of the plurality of electrical signals, wherein the selected portion of the map comprises a set of selected electrical signal representations.

9. The system of claim 1, wherein the processing unit is further configured to:
receive, via the input device, a user input associated with a movement, from a first position to a second position, of the selection indicator;
determine, based on the user input, an additional selected portion of the cardiac map, the additional selected portion comprising an additional set of map locations, each of the additional set of map locations corresponding to an electrical signal of an additional set of electrical signals, the additional set of map locations having a third spatial arrangement, wherein the additional set of electrical signals comprises an additional subset of the plurality of electrical signals; and
facilitating display, via the display, of an additional set of electrical signal representations, each electrical signal representation of the additional set of electrical signal representations corresponding to one of the additional set of electrical signals, the additional set of electrical signal representations comprising a fourth spatial arrangement, wherein the fourth spatial arrangement corresponds to the third spatial arrangement.

10. The system of claim 1, wherein the processing unit is further configured to:
receive, via the input device, a user selection of an additional selected portion of the cardiac map;
determine, based on the user input, an additional selected portion of the cardiac map, the additional selected portion comprising an additional set of map locations, each of the additional set of map locations corresponding to an electrical signal of an additional set of electrical signals, the additional set of map locations having a third spatial arrangement, wherein the additional set of electrical signals comprises an additional subset of the plurality of electrical signals; and
facilitating display, via the display, of an additional set of electrical signal representations simultaneously with the display of the set of electrical signal representations, each electrical signal representation of the additional set of electrical signal representations corresponding to one of the electrical signal set of electrical signals, the additional set of electrical signal representations comprising a fourth spatial arrangement, wherein the fourth spatial arrangement corresponds to the third spatial arrangement.

11. The system of claim 10, wherein the set of electrical signal representations is displayed in a first column and the additional set of electrical signal representations is displayed in a second column, and wherein the second column is displayed adjacent the first column.

12. A method of presenting cardiac information, the method comprising:
receiving a plurality of electrical signals sensed within a patient's heart;
generating, based on the plurality of electrical signals, the cardiac map;
facilitating display, via the display device, of the cardiac map, wherein each of the plurality of electrical signals corresponds to a cardiac map location;
receiving, from an input device, a user selection of a selected portion of the cardiac map;
identifying a set of map locations corresponding to the selected portion;
identifying, for each of the set of map locations, a corresponding electrical signal of a set of electrical signals, the set of map locations having a first spatial arrangement, wherein the set of electrical signals comprises a subset of the plurality of electrical signals; and facilitating display, via the display device, of a set of electrical signal representations, each electrical signal representation of the set of electrical signal representations corresponding to one of the set of electrical signals, the set of electrical signal representations comprising a second spatial arrangement, wherein the second spatial arrangement corresponds to the first spatial arrangement, and wherein the second spatial arrangement is determined by performing a linear scaling operation based on the first spatial arrangement.

13. The method of claim 12, wherein each of the plurality of electrical signals comprises an electrogram.

14. The method of claim 12, further comprising facilitating display, via the display device, of a selection indicator, the selection indicator comprising a representation of the selected portion of the map.

15. The method of claim 12, further comprising:
determining the first spatial arrangement; and
determining, based on the first spatial arrangement, the second spatial arrangement.

16. The method of claim 12, wherein the selected portion of the map comprises at least one of (1) a curve, drawn using the input device, on the cardiac map; (2) a selected region of the cardiac map, and wherein the representation of the selected region comprises a grid having a plurality of grid cells arranged in a plurality of columns and a plurality of rows, wherein each electrical signal of the set of electrical signals has a map location corresponding to one of the plurality of grid cells; and (3) a set of selected electrical signal representations, wherein the cardiac map includes a plurality of electrical signal representations, each of the plurality of electrical signal representations corresponding to one of the plurality of electrical signals.

17. A system for facilitating display of cardiac information, the system comprising:
a display device configured to present a cardiac map; and
a processing unit configured to:
receive a plurality of electrical signals sensed within a patient's heart;
generate, based on the plurality of electrical signals, the cardiac map;
facilitate display, via the display device, of the cardiac map, wherein each of the plurality of electrical signals corresponds to a cardiac map location;
receive, from an input device, a user selection of a first selected portion of the cardiac map, the first selected portion comprising a first set of map locations, each of the first set of map locations corresponding to an electrical signal of a first set of electrical signals, the first set of map locations having a first spatial arrangement, wherein the first set of electrical signals comprises a first subset of the plurality of electrical signals;
receive, from the input device, a user selection of a second selected portion of the cardiac map, the second selected portion comprising a second set of map locations, each of the second set of map locations corresponding to an electrical signal of a second set of electrical signals, the second set of map locations having a second spatial arrangement, wherein the second set of electrical signals comprises a second subset of the plurality of electrical signals; and
facilitate display, via the display, of (1) a first set of electrical signal representations, each electrical signal representation of the first set of electrical signal representations corresponding to one electrical signal of the first set of electrical signals, the first set of electrical signal representations comprising a third spatial arrangement, wherein the third spatial arrangement corresponds to the first spatial arrangement, wherein the third spatial arrangement is determined by performing a linear scaling operation based on the first spatial arrangement; and (2) a second set of electrical signal representations, each electrical signal representation of the second set of electrical signal representations corresponding to one electrical signal of the second set of electrical signals, the second set of electrical signal representations comprising a fourth spatial arrangement, wherein the fourth spatial arrangement corresponds to the second spatial arrangement.

18. The system of claim 17, wherein the first set of electrical signal representations is displayed in a first column and the second set of electrical signal representations is displayed in a second column, and wherein the second column is displayed adjacent the first column.

* * * * *